US008440147B2

(12) United States Patent
Garcia Da Fonseca et al.

(10) Patent No.: US 8,440,147 B2
(45) Date of Patent: May 14, 2013

(54) ANALYTICAL ROTORS AND METHODS FOR ANALYSIS OF BIOLOGICAL FLUIDS

(75) Inventors: João Garcia Da Fonseca, Azambuja (PT); Nuno Alexandre Esteves Reis, Sintra (PT); Robert Burger, Schutteral (DE)

(73) Assignee: Biosurfit, S.A., Aveiro (PT)

( * ) Notice: Subject to any disclaimer, the term of this patent is extended or adjusted under 35 U.S.C. 154(b) by 0 days.

(21) Appl. No.: 13/143,070

(22) PCT Filed: Dec. 30, 2009

(86) PCT No.: PCT/PT2009/000081
§ 371 (c)(1), (2), (4) Date: Sep. 28, 2011

(87) PCT Pub. No.: WO2010/077159
PCT Pub. Date: Jul. 8, 2010

(65) Prior Publication Data

US 2012/0021447 A1 Jan. 26, 2012

(30) Foreign Application Priority Data

Dec. 30, 2008 (GB) .................................. 0823660.6

(51) Int. Cl.
*G01N 15/06* (2006.01)
*G01N 33/00* (2006.01)
*G01N 33/48* (2006.01)

(52) U.S. Cl.
USPC ............ 422/503; 422/50; 422/68.1; 422/502; 422/504

(58) Field of Classification Search .................... 422/50, 422/68.1, 502, 503, 504
See application file for complete search history.

(56) References Cited

U.S. PATENT DOCUMENTS 5,087,532 A 2/1992 Challener, IV
5,414,678 A 5/1995 Challener, IV
(Continued)

FOREIGN PATENT DOCUMENTS

DE 102005048233 4/2007
EP 0608006 5/1991
(Continued)

OTHER PUBLICATIONS

Grumann et al., "Batch-Mode Mixing on Certrifugal Microfluidic Platforms", Lab Chip. 2005. pp. 560-565.

(Continued)

*Primary Examiner* — Brian J Sines
(74) *Attorney, Agent, or Firm* — Patterson Thuente Pedersen, P.A.

(57) ABSTRACT

Devices for generating discrete flow of liquids in response to a driving force, for example centrifugal microfluidic devices for generating discrete flow in response to a constant driving force. The device includes a supply structure for supplying liquid at an inflow rate to a discretization structure in response to a driving force. The discretization structure is shaped to define an outlet and a level to which the discretization structure fills with liquid flowing from the supply structure before dispensing the liquid at an outflow rate through the outlet in response to the driving force. The device is arranged such that the outflow rate from the discretization structure is greater than the inflow rate into the discretization structure, thereby periodically emptying the discretization structure to create a discretized flow from the outlet. The devices find applications in liquid mixing, for example for diluting samples, such as blood plasma samples.

27 Claims, 11 Drawing Sheets

U.S. PATENT DOCUMENTS

| | | | |
|---|---|---|---|
| 5,508,982 | A | 4/1996 | Challener, IV |
| 5,620,792 | A | 4/1997 | Challener, IV |
| 5,639,567 | A | 6/1997 | Challener, IV |
| 5,751,482 | A | 5/1998 | Challener, IV |
| 5,925,878 | A | 7/1999 | Challener |
| 5,955,378 | A | 9/1999 | Challener |
| 5,986,762 | A | 11/1999 | Challener |
| 5,986,997 | A | 11/1999 | Challener, IV |
| 5,994,150 | A | 11/1999 | Challener et al. |
| 6,063,589 | A | 5/2000 | Kellogg et al. |
| 6,100,991 | A | 8/2000 | Challener |
| 6,230,991 | B1 | 5/2001 | Steinruck et al. |
| 6,235,531 | B1 | 5/2001 | Kopf-Sill et al. |
| 6,277,653 | B1 | 8/2001 | Challener et al. |
| 6,320,991 | B1 | 11/2001 | Challener et al. |
| RE37,473 | E | 12/2001 | Challener |
| 6,344,490 | B1 | 2/2002 | DeGeorge et al. |
| 6,625,336 | B2 | 9/2003 | Challener et al. |
| 6,653,152 | B2 | 11/2003 | Challener |
| 6,944,101 | B2 | 9/2005 | Johns et al. |
| 6,944,112 | B2 | 9/2005 | Challener |
| 7,027,700 | B2 | 4/2006 | Challener |
| 7,106,935 | B2 | 9/2006 | Challener |
| 7,266,268 | B2 | 9/2007 | Challener et al. |
| 7,272,102 | B2 | 9/2007 | Challener |
| 7,275,858 | B2 | 10/2007 | Andersson et al. |
| 7,330,404 | B2 | 2/2008 | Peng et al. |
| 7,412,143 | B2 | 8/2008 | Rottmayer et al. |
| 7,440,660 | B1 | 10/2008 | Jin et al. |
| 7,480,214 | B2 | 1/2009 | Challener et al. |
| 7,515,372 | B2 | 4/2009 | Erden et al. |
| 7,580,602 | B2 | 8/2009 | Itagi et al. |
| 7,768,657 | B2 | 8/2010 | Jin et al. |
| 7,796,487 | B2 | 9/2010 | Chu et al. |
| 7,804,656 | B2 | 9/2010 | Gomez et al. |
| 7,830,775 | B2 | 11/2010 | Karns et al. |
| 7,869,162 | B2 | 1/2011 | Lu et al. |
| 7,869,309 | B2 | 1/2011 | Mihalcea et al. |
| 7,893,497 | B2 | 2/2011 | Takasu |
| 2001/0031503 | A1 | 10/2001 | Challener et al. |
| 2003/0053934 | A1 | 3/2003 | Andersson et al. |
| 2003/0128633 | A1 | 7/2003 | Batra et al. |
| 2003/0137772 | A1 | 7/2003 | Challener |
| 2004/0240327 | A1 | 12/2004 | Sendur et al. |
| 2005/0123454 | A1* | 6/2005 | Cox .............................. 422/100 |
| 2005/0157597 | A1 | 7/2005 | Sendur et al. |
| 2005/0217741 | A1 | 10/2005 | Bohm |
| 2006/0233061 | A1 | 10/2006 | Rausch et al. |
| 2007/0115787 | A1 | 5/2007 | Itagi et al. |
| 2008/0170319 | A1 | 7/2008 | Seigler et al. |
| 2009/0207519 | A1 | 8/2009 | Erden et al. |
| 2009/0208171 | A1 | 8/2009 | Gage et al. |
| 2009/0246082 | A1 | 10/2009 | Saiki et al. |
| 2010/0097901 | A1 | 4/2010 | Challener et al. |
| 2010/0123965 | A1 | 5/2010 | Lee et al. |
| 2011/0044147 | A1 | 2/2011 | Karns et al. |
| 2011/0290718 | A1 | 12/2011 | Da Fonseca et al. |

FOREIGN PATENT DOCUMENTS

| | | |
|---|---|---|
| EP | 1684063 | 7/2006 |
| EP | 1900433 | 3/2008 |
| EP | 2080554 | 7/2009 |
| JP | 2004117048 | 4/2004 |
| WO | WO95/33986 | 12/1995 |
| WO | WO97/21090 | 6/1997 |
| WO | WO0146465 | 6/2001 |
| WO | WO03/058641 | 7/2003 |
| WO | WO03060882 | 7/2003 |
| WO | WO03102559 | 12/2003 |
| WO | WO2004003891 | 1/2004 |
| WO | WO2004003932 | 1/2004 |
| WO | WO2004032118 | 4/2004 |
| WO | WO2004107323 | 12/2004 |
| WO | WO2005045815 | 5/2005 |
| WO | WO2007024829 | 3/2007 |
| WO | WO2007091097 | 8/2007 |
| WO | WO2008057000 | 5/2008 |
| WO | WO2008060172 | 5/2008 |
| WO | WO2008/080049 | 7/2008 |
| WO | WO2008106782 | 9/2008 |
| WO | WO2010047609 | 4/2010 |
| WO | WO2010059736 | 5/2010 |
| WO | WO2010077159 | 7/2010 |

OTHER PUBLICATIONS

Haeberle et al., "Certrifugal Micromixer", Chem. Eng. Technology. 2005. pp. 613-616.

Sudarsan et al., "Multivortex Micromixing", Artie McFerrin Department of Chemical Engineering. May 9, 2006. vol. 103, No. 19. pp. 7228-7233.

Nguyen et al., "Micromixers—A Review", Institute of Physics Publishing. Journal of Micromechanics and Microengineering. 2005. pp. R1-R-16.

GB Combined Search and Examination Report for Application No. GB0823660.6 dated May 18, 2009.

GB Response to Search Report for Application No. GB0823660.6 dated Dec. 13, 2010.

International Search Report and Written Opinion for International Application No. PCT/PT2009/000081 dated May 10, 2010.

International Search Report for International Application No. PCT/PT2009/000055 dated Apr. 7, 2010 and Great Britain Search Report for GB Application No. 0819508.3 dated Feb. 26, 2009.

Schomburg et al, "Microfluidic components in LIGA technique" J. Micromech. Microeng. vol. 4, pp. 186-191 (1994).

Ducree et al., "The Centrifugal microfluidic Bio-Disk platform," J. Micromech. Microeng. vol. 17, pp. S103-S115 (2007).

Furlan et al., "Behavior of microfludic amplifiers" Sensors and Actuators. vol. 51, pp. 239-246 (1996).

Furlan et al., "Comparison of Wall Attachment and Jet Deflection Microfluidic Amplifiers" Micro Electro Mechanical Systems, 1996, MEMS '96, Proceedings an Investigation of Micro Structures, Sensors, Actuators, Machines and Systems, IEEE The 9th Annual International Workshop. San Diego, CA pp. 372-377 (Feb. 11, 1996).

Fontana, "Theoretical and Experimental Study of the surface plasmon resonance effect on a recordable compact disk", Applied Optics. vol. 43, No. 7B pp. 79-87 Jan. 1, 2004.

Chiu et al., Calculation of Surface Plasmon Effect on Optical Discs, Jap. J. Appl. Phys. Part 1, vol. 43, No. 7B, pp. 4730-4735 (2004).

International Search Report for International Application No. PCT/PT2011/000009 dated Oct. 18, 2011.

* cited by examiner

ANALYTICAL ROTORS AND METHODS FOR ANALYSIS OF BIOLOGICAL FLUIDS

RELATED APPLICATIONS

The present application is a National Phase entry of PCT Application No. PCT/PT2009/000081, filed Dec. 30, 2009, which claims priority from Great Britain Application No. 0823660.6, filed Dec. 30, 2008, the disclosures of which are hereby incorporated by reference in their entireties.

FIELD OF THE INVENTION

The present invention relates generally to the handling of liquids, in particular but not exclusively to discretization of liquid flow and mixing of liquids, more particularly but not exclusively in a microfluidic device, such as a "lab on a disk" device.

BACKGROUND OF THE INVENTION

Mixing and diluting are essential steps in many assay procedures and constitute important unit operations for lab on a chip or other microfluidic platforms. In particular for point of care applications, mixing and diluting methods need to be fast. In contrast to macroscopic systems where liquid mixing can be achieved by external means such as stirring, shaking or other methods of promoting turbulence in the liquid system, mixing in microfluidic systems is more challenging. Due to the small characteristic dimensions of microfluidic devices the flow is typically laminar and microfluidic mixers have to rely on diffusion and chaotic advection. Several microfluidic mixing principles have been introduced in the past (see, for example, N. T. Nguyen, S. Wu, J. Micromech. Microeng., vol. 15 R1-R16, 2005; A. P. Sudarsan, V. M. Ugaz, PNAS, vol. 103, pp. 7228-7233, 2006). Among these mixers are lamination mixers where liquids are laminated in a common channel to decrease diffusion distances. Mixing can be further enhanced by placing obstacles in the channel or introducing curvatures and abrupt changes in the cross sectional-area of the channels to promote chaotic advection or vortex mixing. Other mixers, especially suited for centrifugal microfluidics explore the coriolis force present in a rotating system to induce secondary flows and promote mixing (see for example S. Haeberle et al, Chem. Eng. Technol., vol. 28, pp. 613-616. 2005) or use periodically changing angular accelerations to perform batch mixing (see for example M Grumann et al, Lab Chip, vol. 5, pp. 560-565, 2005).

SUMMARY OF THE INVENTION

In a first embodiment of the invention, there is provided a device for containing liquid comprising a supply structure for supplying liquid at an inflow rate to a discretization structure in response to a driving force. The discretization structure is shaped to define an outlet and a level to which the discretization structure fills with liquid flowing from the supply structure before dispensing the liquid at an outflow rate through the outlet in response to the driving force. The device is arranged such that the outflow rate from the discretization structure is greater than the inflow rate into the discretization structure, thereby periodically emptying the discretization structure to create a discretized flow from the outlet.

In one embodiment, the device is capable of generating discrete flow in response to a constant or continuous driving force.

As will be described below, the capability of creating discretized or discontinuous flow, that is flow in discrete, temporally separated volumes, finds particular application in liquid mixing applications. However, the invention is not so limited and other applications for the described flow discretization device are equally possible. By adjusting the shape (and/or other properties) of the discretization structure to define a threshold level and a corresponding volume of liquid in the discretization structure, the discrete volume of liquid to be dispensed one at a time can be tuned.

In some embodiments, the discretization structure comprises a conduit in fluidic communication with a liquid supply structure at one end and defining the outlet at the other end. The conduit comprises a bend between the two ends, which defines the threshold level. To achieve a siphon action emptying of the discretization structure once the liquid level exceeds a threshold level, the one end is closer to the bend than the other end. In use, due to the driving force, the bend is therefore at a higher potential than the two ends, with the other end (outlet) being at a lower potential than the one end. The bend thus defines a potential barrier which, once crossed, gives rise to a siphon-like emptying of the discretization structure. Since discretization behavior can be determined by the structure of the device, the device is readily manufactured. For example, the need for particular surface treatments of the fluidic structures of the device can be reduced or avoided.

In some embodiments, the outlet is arranged to provide a surface tension energy barrier to flow of the liquid, thereby retaining liquid in the discretization structure until the liquid reaches the level. At this point, the liquid head acting on the outlet under the influence of the driving force is sufficiently large to overcome the surface tension barrier, so that liquid will flow until the corresponding liquid column breaks and the discretization structure fills again with inflowing liquid, thus providing an alternative mechanism (as compared to the siphon like mechanism described above) for discretising the flow.

The surface tension energy barrier can be provided in a number of ways, for example by introducing a sudden change in dimensions of the outlet to anchor the liquid front or by modifying the surface properties of the structure within or adjacent the outlet or both combined. For example, in an embodiment particularly applicable to handling aqueous solutions in a device manufactured from materials wetted by such solutions (sessile drop contact angle smaller than 90 degrees), the surface tension barrier can be provided by a sudden expansion within or at an end of the outlet (to provide capillary anchoring of the liquid/gas interface) or, alternatively, a hydrophobic surface modification within and/or adjacent the outlet, locally rendering the surface non-wetting to such solutions, which can be combined with a contraction of the structure.

In some embodiments, the conduit comprises a further bend between the one end and the bend and is connected to a volume of the discretization structure filled by the supply structure to favor complete emptying of the volume through the conduit.

In some, "lab on a disk" centrifugal embodiments, the center of rotation defines a co-ordinate system in which the one end is radially outwards of the bend and the other end is radially outwards of the one end. In some such embodiments, the one end is radially outwards of the bend, the other end and further bends are radially outwards of the one end and a port in the volume filled by the supply structure is located at a radially outmost aspect of the volume.

In some embodiments, arranged for liquid mixing of two liquids, the device comprises two supply and discretization structures as described above, one for each liquid, whereby the outlets of the discretization structures are in fluidic communication with a mixing chamber for receiving the two liquids, thereby allowing the liquids to mix.

By injecting the two liquids to mix into the mixing chamber in discrete volumes, the two liquids are intermingled more than if they were simply introduced into the mixing chambers using a continuous flow. The increased intermingling of liquid increases the contact surface between the liquids from each outlet, thereby reducing the diffusion lengths and providing more rapid mixing in the mixing chamber.

This approach enables mixing within a short timescale (typically seconds) by generating an alternating pattern of intermingling fluid volumes of each liquid, thereby reducing the diffusion lengths. Further, the kinetic impact of the discrete liquid volumes on predeposited liquid volumes, further aids mixing. The mixing ratio can be readily controlled using the respective flow rates of each liquid and it is therefore particularly suitable for mixing unequal liquid volumes, which is required for, for example, dilutions.

In some embodiments, the two discretization structures are in fluidic communication with one another inside a common volume, which is only vented by fluidic communication with the mixing chamber (which in turn is connected to an air system of the device or open to atmospheric air). It has been observed that emptying of one of the two discretization structures enhances priming (i.e. the filling of the discretization structure to the level at which dispensing begins) of the other one in this arrangement, thereby encouraging emptying of the discretization structures in alternation one at a time.

In some embodiments, the device comprises an intermediate chamber in fluidic communication with the outlets. The intermediate chamber has a single outlet in fluidic communication with the mixing chamber. Since a single outlet is connected to the mixing chamber, the liquid volume issued from each of the outlets reaches the mixing chamber at the same location through the single outlet, one on top of the other, thus further encouraging mixing.

In some embodiments, the intermediate chamber defines a bubble removing feature adjacent to the outlet of a discretization structure. The feature is arranged such as to capture membranes formed at the outlet after interruption of flow from the outlet as the flow from the other outlet enters the intermediate chamber. If not removed, these membranes could otherwise form bubbles in the discretization structure, inhibiting or even interrupting flow. In some embodiments, the feature is further arranged to guide bubbles formed by successive membranes away from the outlet so that they can dissipate inside the intermediate chamber without inhibiting flow. In some embodiments, the feature is shaped to have a corner adjacent to the outlet and disposed so that the liquid from the other outlet attaches the membrane to the corner as it fills the intermediate chamber. In some embodiments the feature is arranged to extend away from the outlet to define a channel for guiding the bubbles away from the corner. In one embodiment, the channel can widen with distance from the corner, thereby encouraging transit of the bubbles in one direction, away from the corner.

In some embodiment, the supply structures are configured such that the inflow rates to the discretization structures form a ratio corresponding to a pre-determined mixing ratio for given respective liquid properties (e.g. density, viscosity and surface tension), allowing control of mixing ratios. More specifically, the discretization structures of some embodiments are shaped such that the respective volumes issued when the liquids reach the respective threshold level in each of the discretization structures also form a ratio corresponding to the predetermined mixing ratios. In these embodiments, the discrete volumes can issue into the mixing chamber alternatingly.

In some embodiments, the supply structures each comprise a discretization reservoir shaped such that the respective liquid heads change at the same rate when each reservoir is emptied at the corresponding inflow rate. This ensures that the inflow rates have substantially the same time dependency, such that a constant mixing ratio over time can be achieved by design of the shape and location of the supply structures.

In some embodiments, the device comprises a mixing arrangement as described above, wherein the outlet of one of the mixing arrangements is in fluidic communication with one of the discretization structures of the other mixing arrangement, while the other discretization structure of the other mixing arrangement is in fluidic communication with a further supply structure for supplying a further liquid for mixing with the liquids issued from the outlets of the one mixing arrangement. This mixing arrangement thus has a first and second supply structure feeding into the one mixing arrangement, which in turn feeds into the other mixing arrangement. The device further has a third supply structure which feeds into the further mixing arrangement. Thus liquids from the first and second supply structures are mixed with liquid from a third supply structure in the other mixing arrangement.

In some embodiments, the second and third supply structure include a common aliquoting structure for aliquoting respective volumes of the second and third liquid from a common reservoir. The second and third liquids are thus the same and in this embodiment, and the device provides a two step dilution of the liquid from the first supply structure with a dilutant from the common reservoir.

In some embodiments, the first supply structure comprises means for receiving a blood sample and separating the blood plasma from it, as well as providing the separated blood plasma as the first liquid, to be diluted by a dilutant.

In some embodiments the device is a microfluidic device, for example defining an axis of rotation and rotatable about the axis to provide the driving force. Such centrifugal microfluidic devices are commonly referred to as “lab on a disk” devices. In some embodiments, the device is disk-shaped.

In a further embodiment of the invention, there is provided a method of separating and diluting blood plasma from a blood sample including loading the blood sample into a supply structure of a device as described above, comprising blood separating means, spinning the device to separate the blood plasma and stopping the device before spinning it again to dilute the separated blood plasma with a dilutant.

In yet a further embodiment of the invention a method of manufacturing a device as described above is provided, having predetermined inflow rates to the discretization structures for a given driving force, wherein the supply structures include a reservoir and conduit connecting the reservoir to the respective discretization structure. The method includes designing the configuration and layout of the reservoir and conduit in accordance with the corresponding predetermined inflow rates and manufacturing the device in accordance with the designs. In one embodiment, by adapting the length and/or cross sectional area of the conduit to tune the hydraulic resistance in accordance with the corresponding predetermined inflow rates, the manufacturing complexity can be reduced.

Yet further embodiments of the invention, provide various devices and systems for discretising flow of liquid, mixing liquids and mixing liquids in a multi-stage, cascaded fashion (using two or more sequential mixing arrangements which are as described above or, instead or additionally, using any other suitable mixing arrangement).

BRIEF DESCRIPTION OF THE DRAWINGS

Embodiments of the invention are now described by way of example only and for the purpose of illustration, with reference to the accompanying drawings, in which.

DETAILED DESCRIPTION OF THE DRAWINGS

Figure 1A:
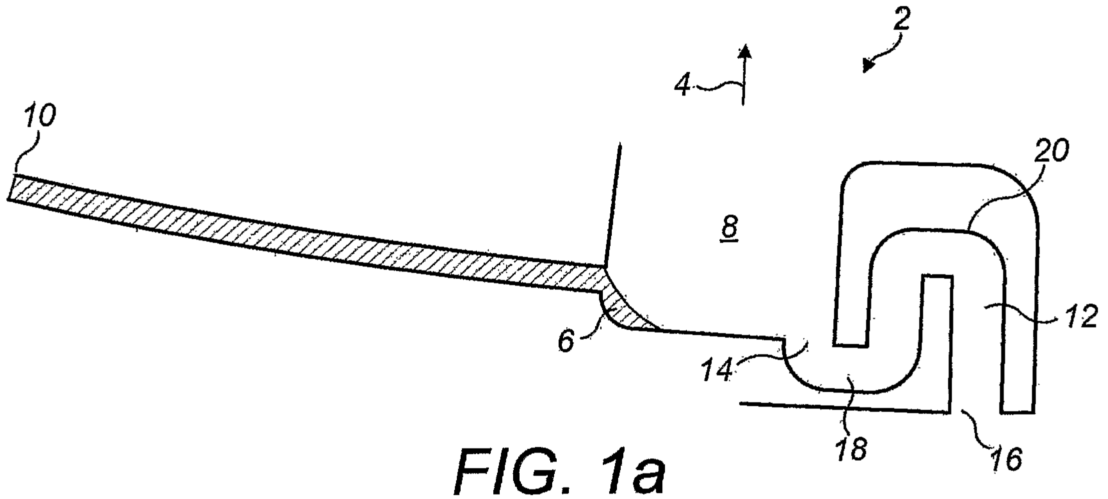
FIGS. 1*a* to 1*d* illustrate basic principles underlying a discretization structure.

Referring to FIGS. 1*a* to 1*d*, a discretization structure (2), that is a structure for discretising liquid flow, a "lab on a disk" microfluidic device having a center of rotation with a location indicated by an arrow (4) is now described. The discretization structure defines a volume (8) for receiving a liquid (6) from a supply structure (10).

A siphon like arrangement of the discretization structure (2) comprises a conduit (12) having an inlet port (14) through which the liquid (6) from the volume (8) can enter the conduit (12). The conduit (12) has an outlet (16) located radially out from the inlet (14) so that the outlet is at a lower centrifugal potential than the inlet when the device is rotated. The conduit defines a first bend (18) radially outward from the inlet (14) to allow the conduit (12) to be connected to the volume (8) at its radially outmost aspect to aid draining of the volume (8). A second bend (20) of the conduit, radially inward from both the inlet (14) and the outlet (16), is located between the first bend and the outlet, thereby providing a potential barrier between the inlet and the outlet when the device is rotated.

Figure 1B:
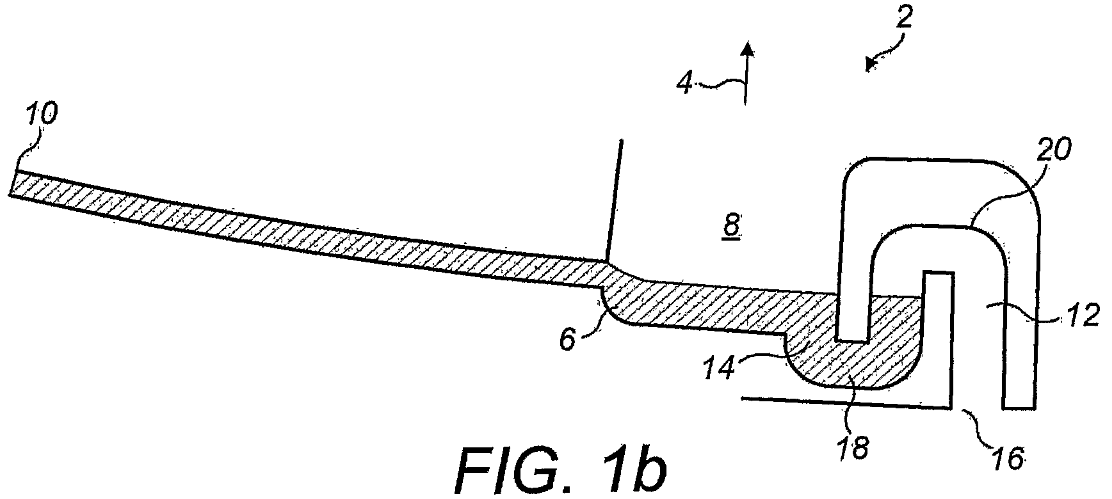
Figure 1C:
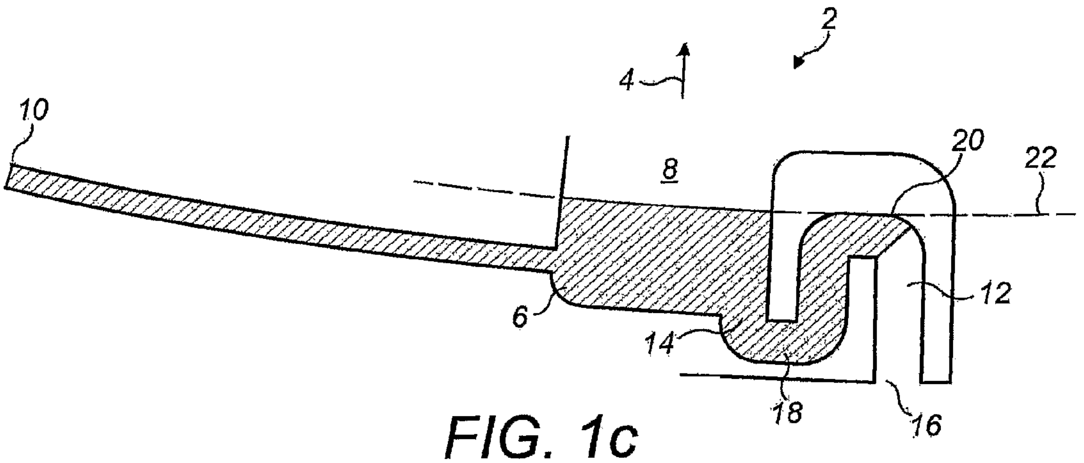
Figure 1D:
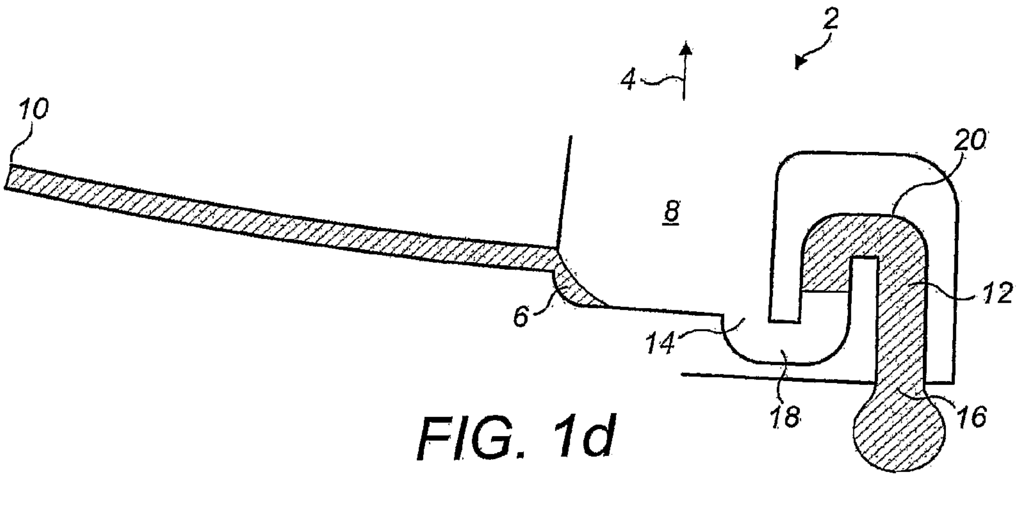

In use, as the microfluidic device rotates, the liquid (6) flows from the supply structure (10) into the volume (8) under the influence of the centrifugal force and begins to fill both the volume (8) and the conduit (12). As long as the liquid has not crossed a threshold level (22) corresponding to the potential barrier provided by the second bend, as illustrated in FIG. 1*b*, no liquid is dispensed from the outlet (16). As the liquid (6) crosses the threshold level (22), as illustrated in FIG. 1*c*, the centrifugal force urges the liquid towards the outlet (16), at the lowest potential of the discretization structure (2). From this point, liquid will continue to be issued from the outlet (16) due to a siphon effect as long as the conduit (12) is not vented and the disk rotates.

The supply structure (10) and the discretization structure (2) are arranged such that the inflow rate of liquid from the supply structure (10) is lower than the outflow rate of liquid from the outlet (16). Thus, once liquid starts flowing from the outlet (16), the level of the liquid (6) in the volume (8) will decrease from the threshold level (22) at which the potential barrier is crossed until the volume (8) is drained so that the inlet (14) is exposed to air, at which point the conduit (12) is vented and the remaining liquid in the conduit is dispensed from the outlet (16). At this stage the volume (8) will continue to fill again as the potential barrier provided by the bend (20) again prevents liquid from being issued through the outlet, thus recommencing the sequence described above.

It can thus be seen, that, under the influence of a continuous driving force such as a continuous centrifugal force, the described discretization structure issues discrete volumes of liquid in a periodic fashion. The discrete volume being issued is determined by the volume of liquid inside the volume (8) and the conduit (12) corresponding to the threshold level (22) (ignoring any amounts of liquid remaining in the volume (8) after each cycle).

Figure 2A:
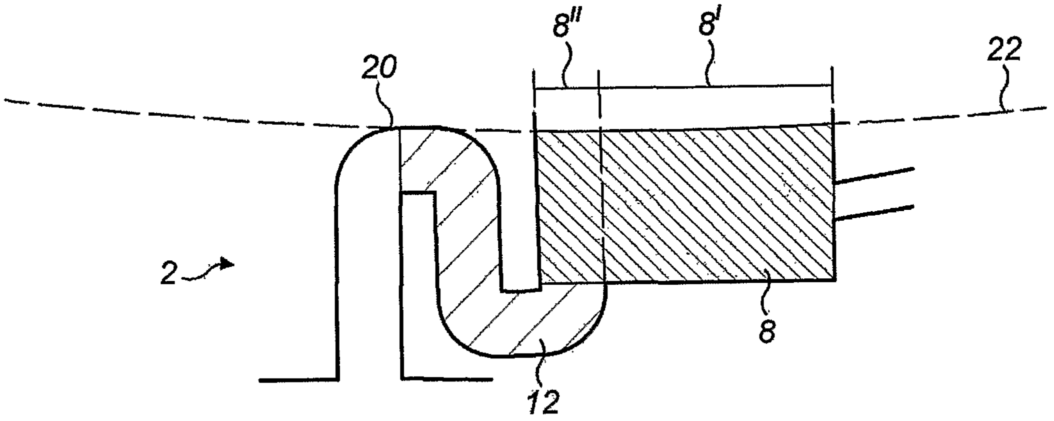
FIGS. 2*a* and 2*b* illustrate one way of varying the discrete dispensed volumes.
Figure 2B:
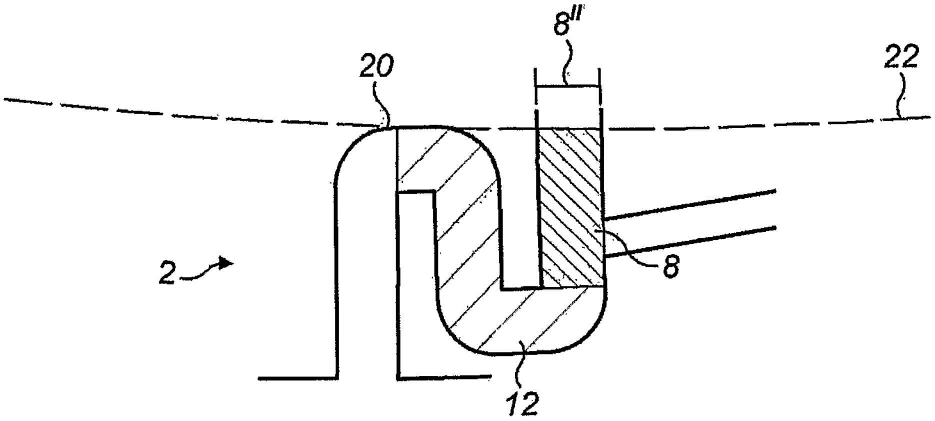

With reference to FIGS. 2*a* and 2*b*, one way of varying the discrete dispensed volume is now described. In FIG. 2*a*, as in FIG. 1*a* to 1*d*, the discrete volume is determined by the volume inside the conduit (12) and the volume (8) at the liquid level (22) before the potential barrier due to the bend (20) is crossed. With reference to FIG. 2*b*, the volume (8) dispensed is reduced by, in effect, eliminating the separate chamber (8'), leaving the prolongation (8") of the conduit (12) to define the volume (8), with the equivalent considerations otherwise applying.

As described above, the discretization structure relies on the inflow rate of liquid into the discretization structure being less that the outflow rate from the discretization structure. Thus, it is required to tune the respective rates accordingly. This is now described with reference to FIG. 3.

Figure 3:
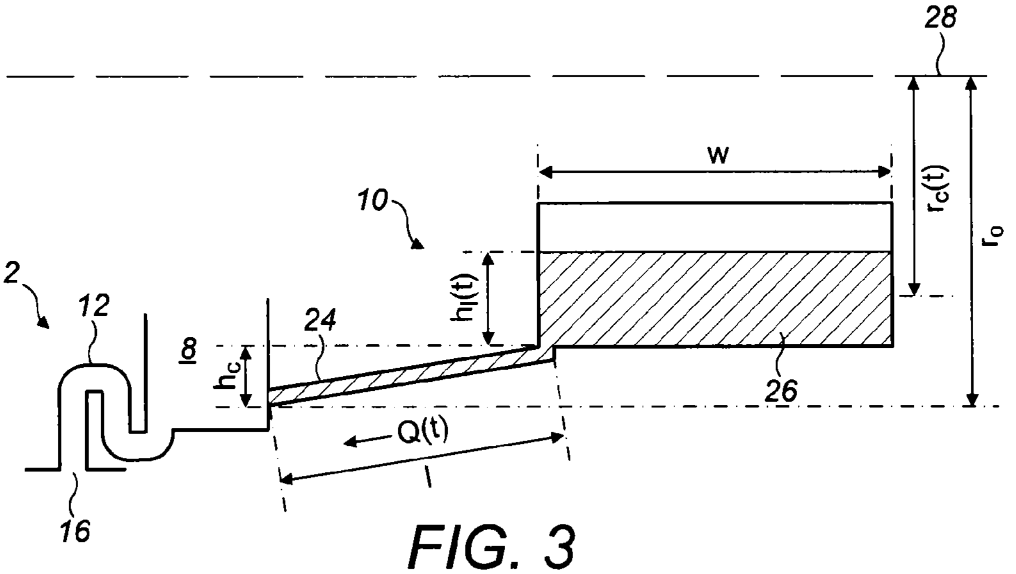
FIG. 3 illustrates a supply structure connected to a discretization structure and design considerations influencing flow rates.

FIG. 3 depicts a developed view of a centrifugal discretization structure (2) connected by a conduit (24) to a supply reservoir (26), the center of rotation being indicated, in the developed view, by the dashed line 28. The flow rate will depend on the driving pressure and resistance of the flow path which in turn depends on a number of factors such as the length and cross section of the flow path and on the fluidic properties (such as density and viscosity) of the liquid flowing through the flow path. For example, the correct relationship of the in and outflow rates is readily achieved by making a supply conduit (24) of the supply structure (10) longer than the flow path from the volume (8) through the conduit (12) to the outlet (16), all other factors being equal. Other, alternative or additional arrangements, such as making the conduit (12) wider than the conduit (24) are used in some embodiments.

For mixing arrangements described below, it is desirable to tune the inflow rate into the discretization structure. FIG. 3 shows a simplified model of a flow discretization structure (2), which is connected to a radially more inwards supply reservoir (26) by a channel (24) with length 1. When the disk is spinning, the centrifugal force acts on the liquid in the reservoir (26). This force generates a pressure, which leads to a liquid flow Q through the channel (24) towards the discretization structure (2). The flow rate of a pressure driven flow through a channel is given by the Hagen Poiseuille equation:

$$Q_v(t) = \frac{\Delta P_v(\omega, t)}{R_{hd}} \quad \text{(eq. 1)}$$

with: $Q_v(t)$=volume flow rate $\Delta P_v(\omega, t)$=centrifugally induced pressure $R_{hd}$=hydrodynamic flow resistance For the sake of simplicity, the counter pressure created by the liquid accumulating in the discretization chamber is neglected. Therefore $\Delta P_v(\omega, t)$ is now referred to as $P_v(\omega, t)$. The pressure created by the centrifugal force depends on the angular velocity ω and since the liquid level in the reservoir decreases over time, it is also time dependent. This pressure is given by:

$$P_v(\omega,t)=\rho_l\cdot\omega^2\cdot r_c(t)\cdot h(t) \quad \text{(eq.2)}$$

with: $\rho_l$=density of the liquid $r_c(t)$=radial distance from the center of rotation of center of mass of the liquid column h(t)=radial length of the liquid column The radial distance $r_c$ is given by:

$$r_c(t) = r_0 - \frac{h(t)}{2} \quad \text{(eq. 3)}$$

with: $r_o$=radial distance from center of rotation to the end of the conduit.

According to FIG. 3, the radial length h(t) of the liquid column is given by:

$$h(t)=h_l(t)+h_c \quad \text{(eq.4)}$$

with: $h_l(t)$=time dependent liquid height in the reservoir $h_c$=radial length of the inclined outlet channel The time dependent radial length of the liquid in the reservoir $h_l(t)$ can be calculated as $$h_l(t) = h_l(t-\Delta t) - \frac{Q_v(t-\Delta t)\cdot\Delta t}{w\cdot d} \quad \text{(eq. 5)}$$

with: w=width of the reservoir d=depth of the reservoir

Besides the time dependent liquid level in the reservoir, the flow rate is, according to Equations 5 and 1, also determined by the time independent hydrodynamic resistance of the outlet channel. To a first approximation this resistance only depends on the channel geometry and the viscosity of the fluid and can be estimated for channels with rectangular cross section as $$R_{hd} = \frac{8\cdot(1+A_r)^2\cdot\eta\cdot l}{A_r\cdot A^2} \quad \text{(eq. 6)}$$

with: A=cross section area of the channel $A_r$=aspect ratio of the channel

η=viscosity of the liquid l=channel length

The equations described above illustrate the dependency of the inflow rate to the discretization structure (2) on the geometry (shape, location relating to the center of rotation and dimensions) of the supply structure relative to the center of rotation and the discretization structure, as well as the shape and configuration of its various components. It has been found experimentally that this simple model provides a good description of the flow rates in the discretization structures in the mixing arrangements now described. In some embodiments, this model is being used to determine design parameters of the device, for example by simulating the equations and varying the design parameters, to provide desired discrete volumes and dispensing or flow rates.

Figure 4:
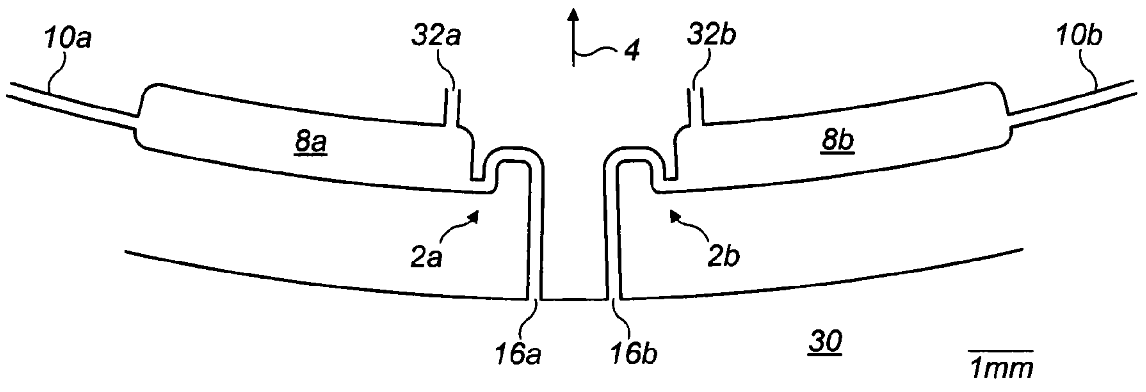
FIG. 4 illustrates a mixing arrangement using the discretization structure.

With reference to FIG. 4, a mixing arrangement comprising two discretization structures (2*a*) and (2*b*), as described above is now described. The two discretization structures (2*a*) and (2*b*) are each supplied with a respective liquid from a respective supply structure (10*a*) and (10*b*) and are connected at the outlets (16*a*) and (16*b*) to a mixing chamber (30). Each of the discretization structures comprises an individual vent connection (32*a*) and (32*b*) to the air system of the device (or open to atmospheric air) for the volumes (8*a*) and (8*b*) to be vented. In use, discrete volumes of the respective liquids are issued periodically from each of the outlets (16*a*) and (16*b*) into the mixing chamber as described above. Since discrete volumes of liquid are issued into the mixing chamber, the two liquids are more intermingled than if they were issued in bulk, one after the other. Further, the repeated impact of liquid issuing from the outlets (16*a*) and (16*b*) further aids mixing.

Figure 5:
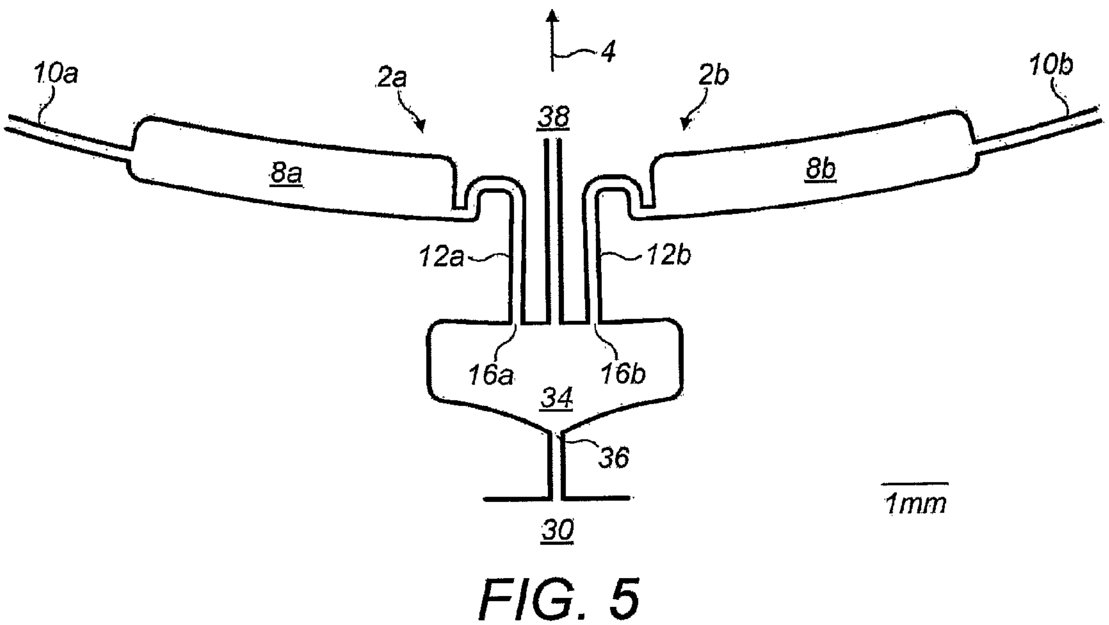
FIG. 5 illustrates another mixing arrangement having a common intermediate reservoir issuing into a mixing chamber.

With reference to FIG. 5, an alternative mixing arrangement is described in which the outlets (16*a*) and (16*b*) are each connected to an intermediate chamber (34) which in turn has a single outlet (36) to the mixing chamber (30). In use, the operation is the same as described above for FIG. 4 but liquid from the outlets (16) impact the mixing chamber (30) in approximately the same location determined by the position of the single outlet (36), so that subsequent discrete volumes are issued into the mixing reservoir (30) on top of each other to further improve mixing. It is further believed that a certain amount of mixing occurs inside the intermediate chamber (34). Instead of the individual vent connections (32), this arrangement has a single vent connection (38) into the intermediate chamber (34) so that the volume (8) of the discretization structures (2*a*) and (2*b*) are vented through the outlet (16) once the conduit (12) has emptied.

Figure 6:
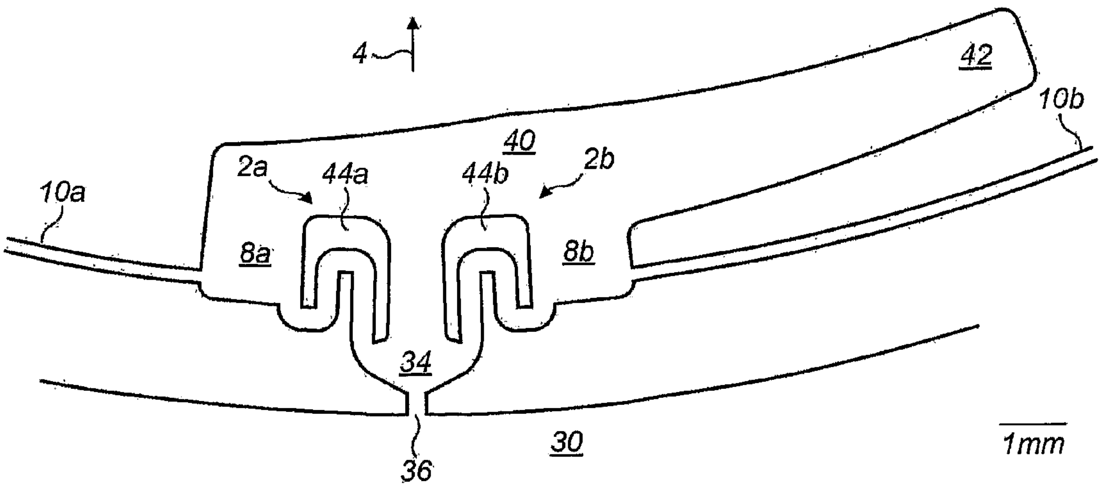
FIG. 6 illustrates yet another mixing arrangement in which the discretization structures are in fluidic communication in a common volume.

With reference to FIG. 6, a further mixing arrangement also comprises an intermediate chamber (34) but the discretization structures (2*a*) and (2*b*) are provided in a common chamber (40) (which can optionally comprise an air buffer space (42)). The discretization structures (2*a*) and (2*b*) are defined co-operatively by the shape of the chamber (40) and a respective shaped feature (44*a*) and (44*b*) for each discretization structure. The intermediate chamber (34) forms part of the common chamber (40) and is defined by a part of its contour. The common chamber (40) does not have a separate vent port, so that the discretization structures (2*a*) and (2*b*) can only be vented through the single outlet (36) and the mixing chamber (30), which is in turn connected to an air system of the device or open to atmospheric air. In practice, this arrangement has been found to increase the reliability of an alternating sequence of issuing discrete volumes from each of the discretization structures (2*a*) and (2*b*), such that the intermingling of the discrete volumes in the mixing reservoir is maximized as successive volumes issued into the reservoir are substantially synchronized so that they are alternatingly issued from the discretization structures (2*a*) and (2*b*).

Figure 7:
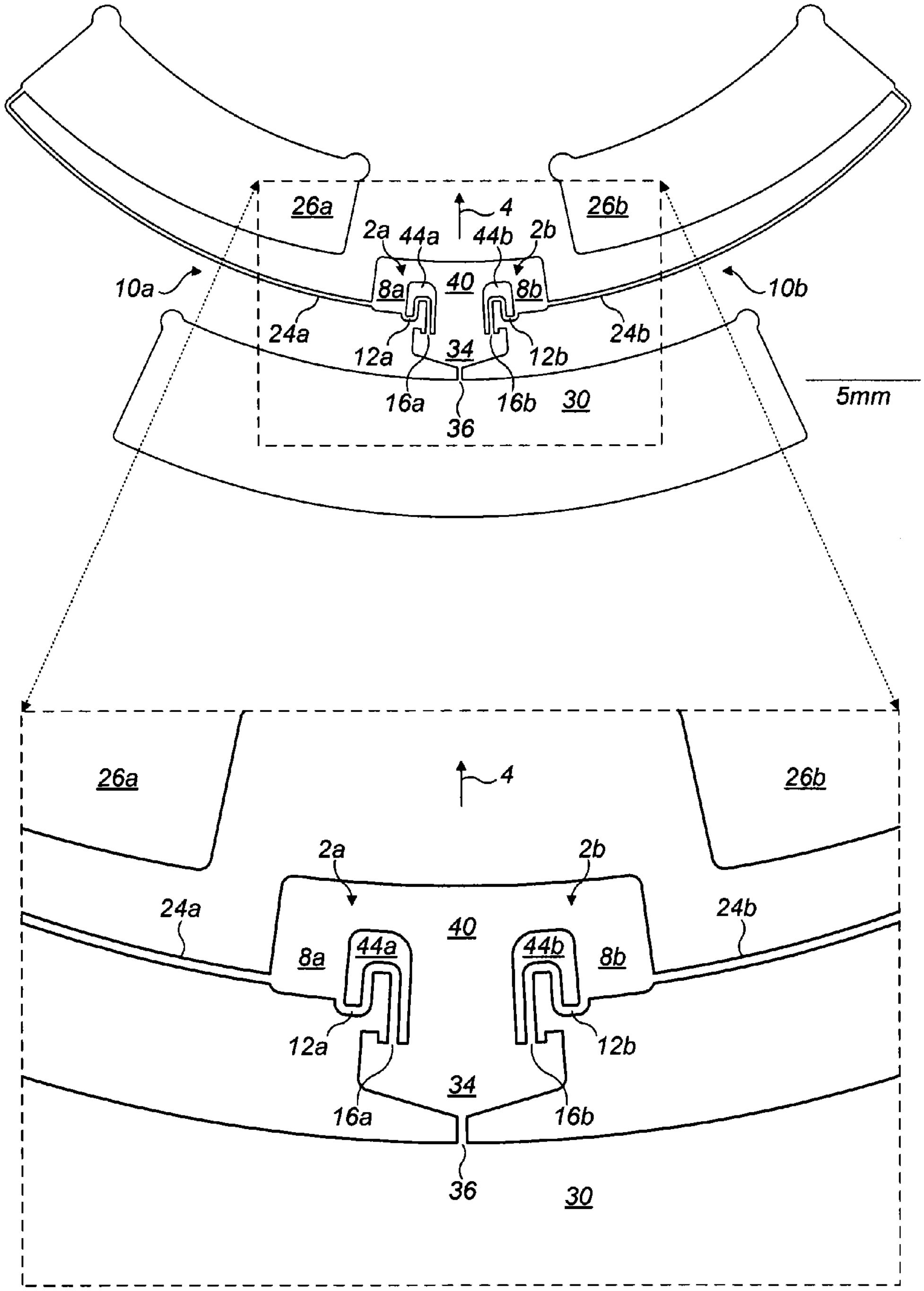
FIG. 7 illustrates a "lab on a disk" mixing arrangement including supply and discretization structures and a mixing chamber.

A complete system for mixing two equal liquid volumes of substantially the same liquid properties in a mixing ratio of 1(or otherwise in a mixing ratio determined by the respective liquid properties) is now described with reference to FIG. 7. Two respective reservoirs (26*a*) and (26*b*) are connected by corresponding conduits (24*a*) and (24*b*) to respective discretization structures (2*a*) and (2*b*), each of which issues into the intermediate chamber (34) and then through the single outlet (36) into the mixing chamber (30). The conduits (24*a*) and (24*b*) are dimensioned to present a hydraulic resistance larger than the conduits (12*a*) and (12*b*) to achieve an inflow rate lower than the outflow rate, as described above. The reservoirs (26*a*) and (26*b*) and the conduits (24*a*) and (24*b*) are symmetrical about a central axis of the mixing arrangement, resulting in a ratio in flow rates determined by a ratio of the respective liquid properties (1 for equal properties). For the sake of clarity a mixing ratio of 1 means that one unit volume of each liquid are mixed giving a total of two unit volumes. This corresponds to a dilution of 1:2.

In addition to mixing two liquids in a mixing ratio of 1 (or determined by their liquid properties), arbitrary mixing rates can be achieved, taking account of the respective properties of the liquids by adjusting the inflow rates into each of the discretization structures (2*a*) and (2*b*). As described above with reference to FIG. 3, equations (1) to (6) provide a relationship between geometric factors, rotational frequency (or other driving force), liquid properties and the resulting flow rates. Accordingly, for each liquid and corresponding supply structure, the geometric factors in equations (1) to (6) can be tuned to achieve the desired respective flow rates.

In some embodiments, one or more of the width and depth of the conduit (24), the radial location of the reservoir (26) or the length of the conduit (24) are factors tuned to achieve the desired flow rates. In particular, the length of the conduit (24) is an advantageous factor to tune in many embodiments as it can readily be altered in many production methods maintaining substantially the same production parameters. This is contrasted with tuning the width and/or depth of the conduit, which in many cases can increase the production complexity to achieve differentiated conduit cross sections in order to achieve the desired flow rates.

The equations described above are used in some embodiments to set up a simulation of each supply structure and its corresponding flow rate, allowing calibration curves to be obtained providing a resulting flow rate as a function of, for example, conduit lengths. These curves (or direct simulation) are then used to design an appropriate structure providing the desired flow rates for the liquids (having each their specific viscosity) and then to manufacture a corresponding device using the techniques described below. While the mixing ratio of the liquids is primarily determined by the respective flow rates described above, if a flow behavior is desired in which the discrete issuance of volumes from the discretization structures is synchronized so that the same number of discrete volumes is issued from each discretization structure per unit of time, the threshold volumes corresponding to the threshold levels, (or, more precisely, the volumes dispensed in each cycle) are designed in direct proportion to the respective flow rates, for example, adapting the discretization structure as described above with reference to FIGS. 2*a* and 2*b* or below with reference to FIG. 8.

In order to achieve a mixing ratio which is constant over time as the reservoirs containing the respective liquids empty (synchronous mixing), it is required that the liquid heads in each reservoirs change at respective rates corresponding to the mixing ratio. For mixing equal volumes of liquids exhibiting identical fluidic properties this can be achieved by ensuring that the reservoirs have the same cross sectional area (across the liquid head) for the same height of the liquid column within each reservoir and simultaneously the downstream conduits and discretization structures are identically shaped. For other mixing ratios and/or mixing of liquids of different properties, adjustments to the geometry and dimensions of each fluidic structure are required to ensure synchronous mixing, since the fluid propulsion mechanism on either side of the structure is the same. Typically, this is achieved by designing the structure to tune the flow rates on either side of the mixing arrangement to enable: (a) an alternating sequence of consecutive droplets of either liquid with a volume ratio corresponding to the mixing ratio or; (b) to generate a sequence of discrete identical volumes in which one of the liquids is issued consecutively before alternating to the other liquid, in a issuing ratio corresponding to the mixing ratio or, (c) a combination of these two modes of operation.

Figure 8:
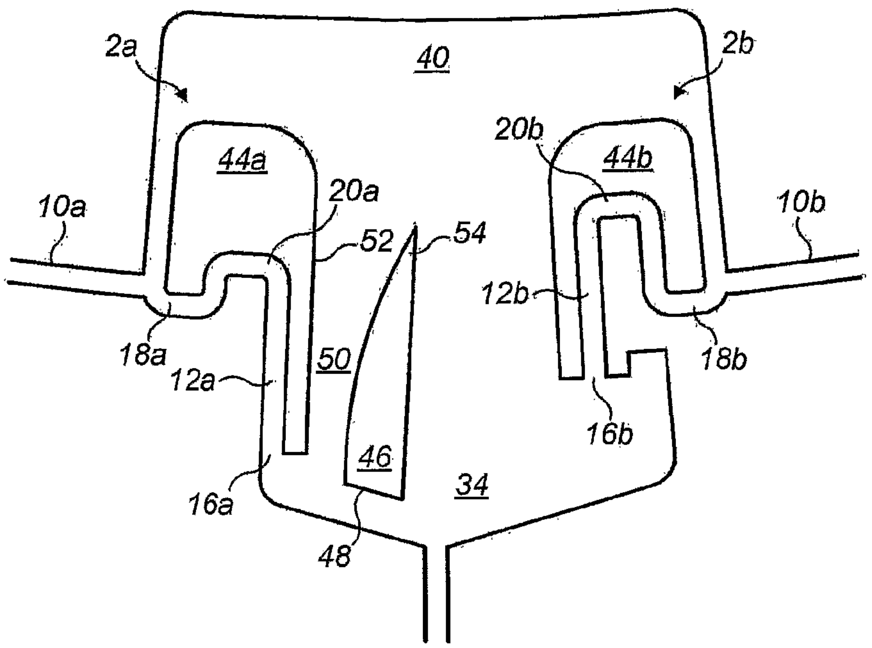
FIG. 8 illustrates a bubble removal feature.

With reference to FIG. 8, a discretization structure (2*a*) in a mixing arrangement as described above with reference to FIGS. 6 and 7 is now described which, together with a bubble removing feature (46) inside the common chamber (40), is adapted for discretizing flow of liquids having propensity to form bubbles as successive discrete volumes are issued from the outlet (16*a*). The bubble removing feature (46) is disposed adjacent to the feature (44*a*) such that a corner (48) of the feature (46) is disposed adjacent to the outlet (16*a*) and radially such that the corner (48) is contacted by liquid issued from the other discretization structure (2*b*) inside the common volume (40). The discretization feature (46) extends radially inward from the corner (48) in a direction generally along the direction of a medial wall (52) of the feature (44). A wall (54) of the feature (46) facing the medial wall (52) is shaped to slope away from the medial wall (52) as it extends from the corner (48), thereby defining an expanding passage between the walls (52) and (54) to define a bubble chimney or conduit, as described below.

Figure 9A:
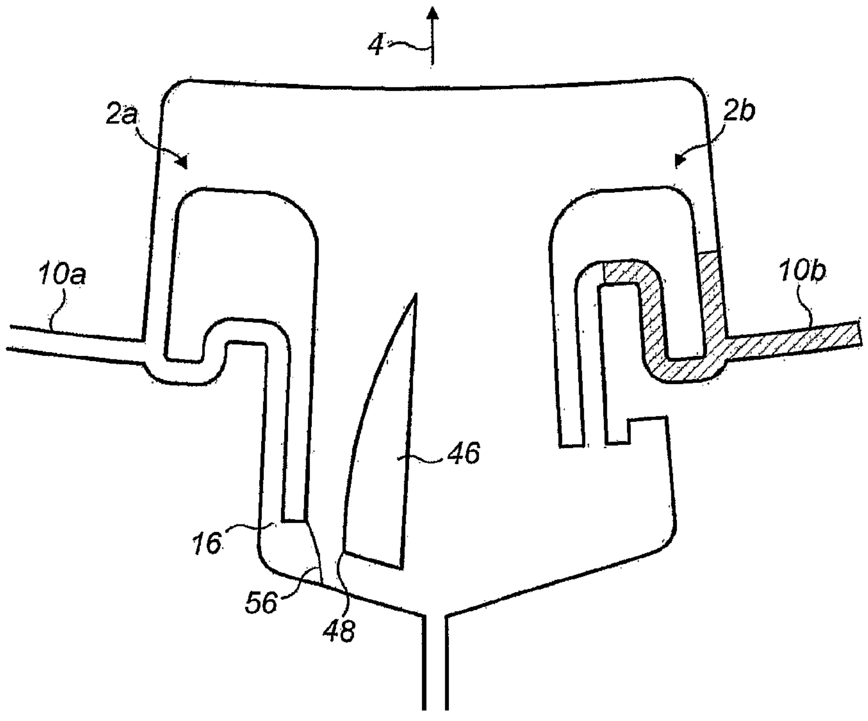
FIGS. 9*a* to 9*c* illustrate the operation of the bubble removal feature.
Figure 9B:
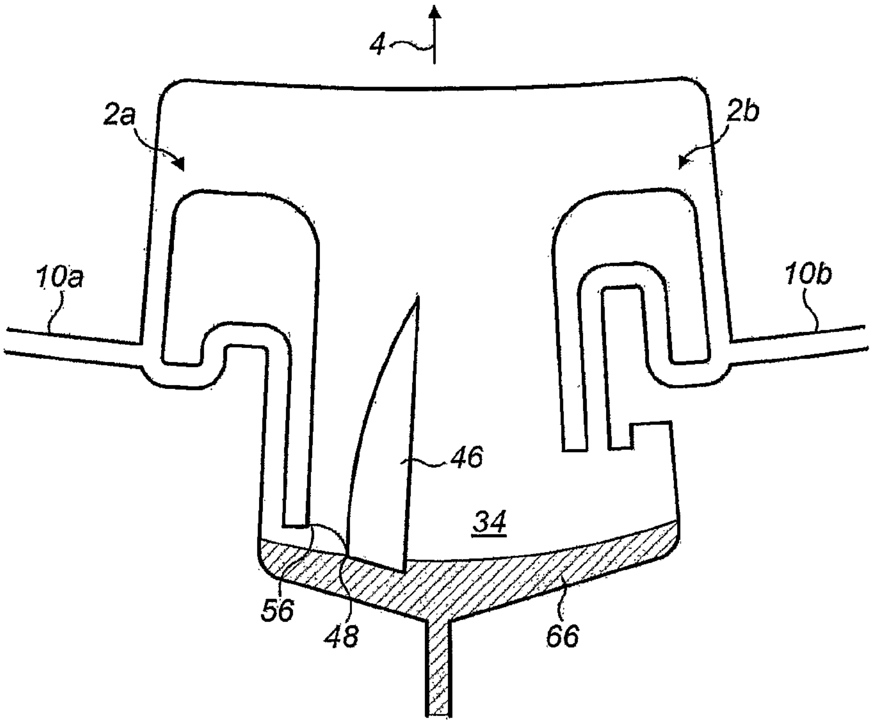
Figure 9C:
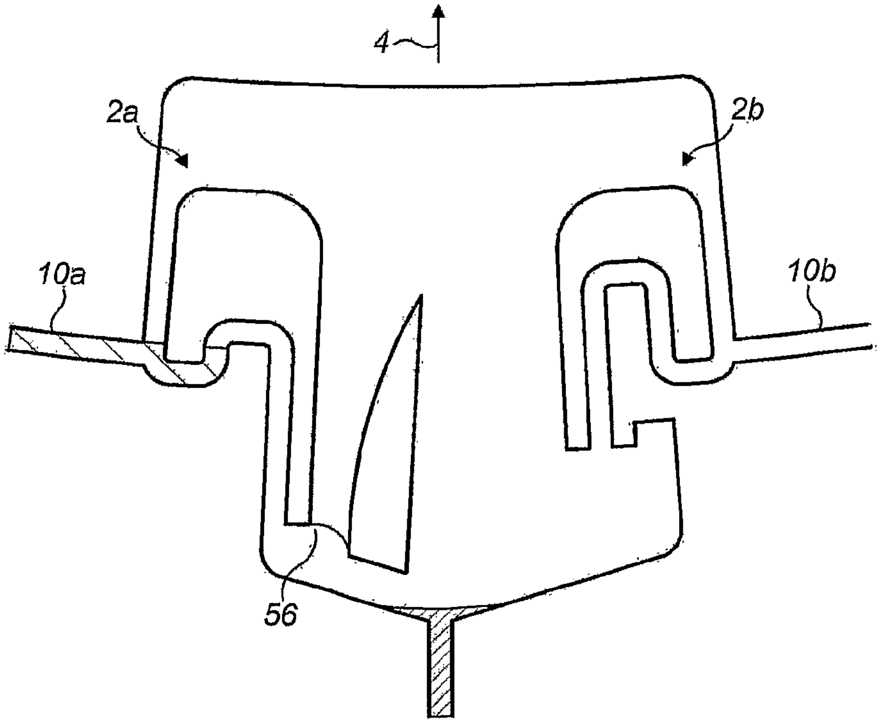

The operation of the bubble removing feature (46) is now described with reference to FIGS. 9*a* to 9*c*. FIG. 9*a* depicts the mixing arrangement at a point in time where a discretized volume of liquid has just issued from the discretization structure (2*a*). Due to the intrinsic fluidic properties of the liquid issued from the discretization structure (2*a*), a membrane (56) is formed after a cessation of flow due to surface tension. FIG. 9*b* depicts the mixing arrangement at a point in time at which, subsequently, a discrete volume of liquid has just issued from the other discretization structure (2*b*). The liquid level inside the intermediate chamber (34) of liquid (6*b*) issued from the discretization structure (2*b*) is at a level where it reaches the corner (48) of the feature (46). As a result, the membrane (56) is carried by the liquid (6*b*) to attach to the corner (48) due to surface tension effects. The abrupt change of curvature of the feature (46) at the corner (48) aids this attachment. Subsequently, the liquid (6*b*) drains from the intermediate chamber (34) leaving the membrane (56) attached to the corner (48) (see FIG. 9*c*). A subsequent repetition of this cycle will each attach a further membrane (56) to the corner (48), forming a bubble in the passage between the walls (54) and (52). Due to the radially inward expanding shape of this passage, the bubbles are urged radially inward, away from the outlet (16*a*) to dissipate in a radially inward portion of the common chamber (40). As the formed bubbles are transported away from the outlet (16*a*), interference of the formed bubbles with flow from the discretization structure (2*a*) is reduced or even prevented.

With reference, again, to FIG. 8, a further way of adjusting the volume of the dispensed liquid from the discretization structures is described. As can be seen in FIG. 8, the radial excursion of the conduit (12*a*), as defined by the distance between the two bends (20) and (18) is less than the radial excursion for the conduit (12*b*) and, accordingly, the threshold volume inside the discretization structure corresponding to the threshold level (22) is larger in the discretization structure (2*b*) than that in the discretization structure (2*a*). This provides an alternative way of adjusting the dispensed volume, in addition to the above discussion with reference to FIGS. 2*a* and 2*b*.

Figure 10:
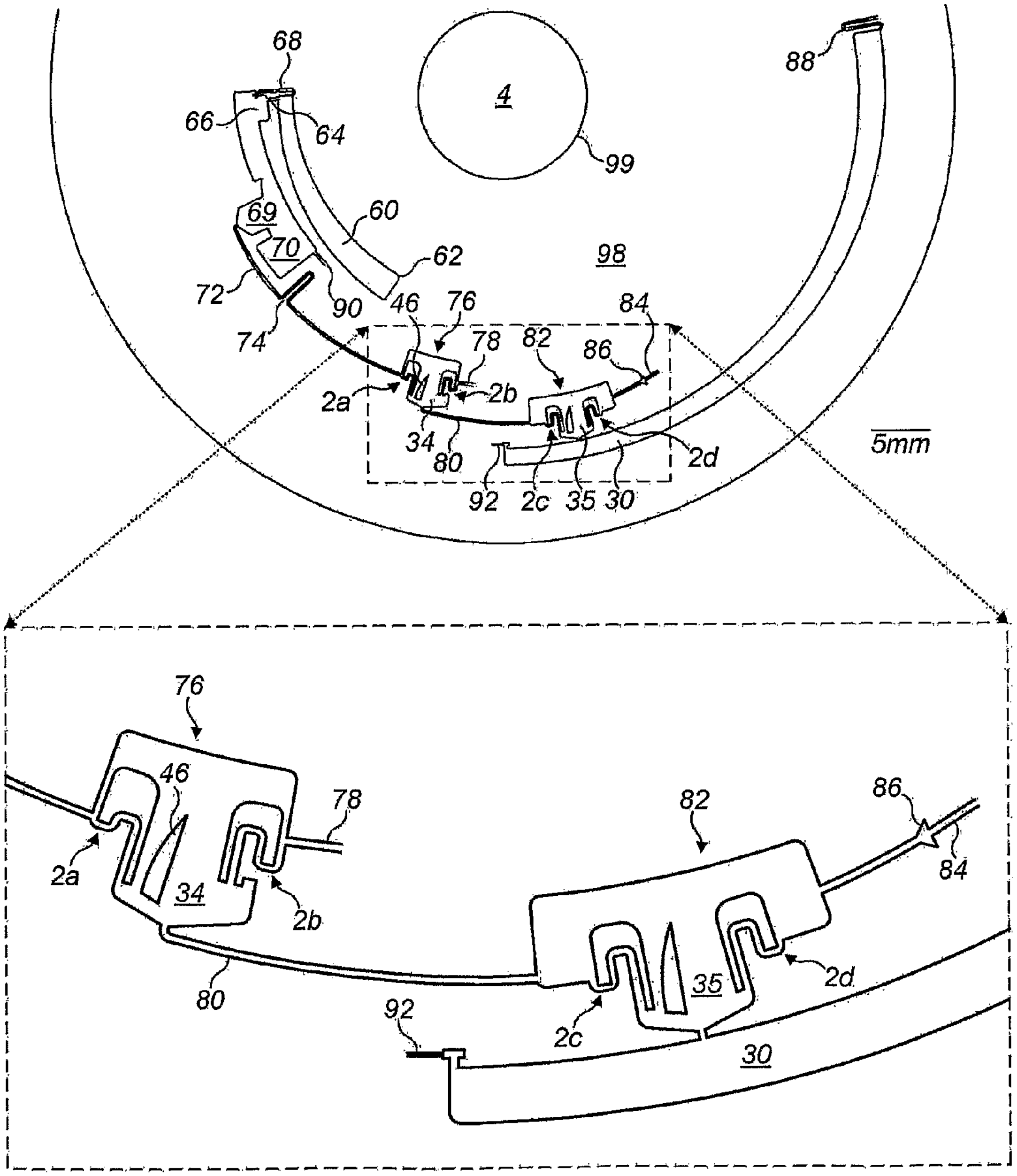
FIG. 10 illustrates an integrated "lab on a disk" system including a blood separation structure and two sequential mixing structures issuing into a mixing chamber.

With reference to FIG. 10, an integrated system using a two stage dilution arrangement to dilute a sample, such as a blood plasma sample separated from a blood sample, in an integrated structure is now described. A separation chamber (60) has a sample inlet (62) and an outlet (64) leading into a receiving chamber (66). The receiving chamber (66) is vented back to the separating chamber (60) by the vent (68). The opening of the vent (68) into the receiving chamber (66) is adjacent with the opening of the inlet (64) into the receiving chamber (66). The height of the receiving chambers (66) (perpendicular to the plane of the Figure) is arranged so that liquid entering through the inlet (64) forms a liquid membrane across the receiving chamber (66).

In use, the separating chamber (60) is isolated from outside atmospheric air by closing the blood inlet (62) (for example using an adhesive flap) and the receiving chamber (66) is in fluidic communication with outside air through an air system connection (90) opposite the opening of the vent (68) from the opening of the inlet (64). As the liquid level in the separation chamber (60) drops when liquid flows through the inlet (64) to the receiving chamber (66) in response to a centrifugal driving force as the device is rotated at a first speed, a negative pressure is created in the separating chamber (60), attracting the membrane of liquid in the receiving chamber (66) into the vent (68) until a liquid plug is formed in the vent (68) At this stage, the vent connection (68) is blocked and flow through the inlet (64) seizes so that the blood sample remains in the separating chamber (60) and separates into plasma and cellular material under the influence of the centrifugal force.

A portion of the separating chamber (60) is arranged to be radially beyond the separating chambers (60) connection to the inlet (64) so that the separated cellular material remains inside the separating chamber (60) as flow through the inlet (64) is re-established. This is achieved by a change in the speed of rotation of the device to dislodge the liquid plug from the vent (68). The receiving chamber (66) is in fluidic communication with a metering structure (69) and shaped so that blood plasma flows from the receiving chamber (66) to the metering structure (69) while at the same time retaining remaining cellular components. The metering structure (69) is in fluidic communication with the overflow structure (70) such that a defined volume is retained in the metering structure (69) with any excess plasma flowing into the overflow structure (70).

The metering structure (69) is connected by a conduit (72) to a first discretization structure (2*a*) of a mixing arrangement (76). The mixing arrangement (76), in some embodiments, as described above with reference to FIG. 8, includes a bubble removing feature (46) for removing bubbles from blood plasma, although other mixing arrangements as described above or any other suitable mixing arrangements, are used in other embodiments. The conduit (72) defines a capillary siphon (74) arranged to stop flow in the conduit (72) past the capillary siphon (74) due to centrifugal pressures acting on the liquid column in the capillary siphon (74), as the device is rotated, and, as the device is stopped or slowed down sufficiently, to draw liquid past the capillary siphon (74) due to capillary action. Once liquid has been drawn past the radially innermost level of liquid in the metering chamber (69), rotation of the device can be resumed to draw the liquid using a siphon effect. Thus, the capillary siphon (74) acts as a valve blocking flow as the device is initially rotated, which can be opened by briefly stopping or slowing rotation of the device.

The other discretization structure (2*b*) of the mixing arrangement (76) is connected to a reservoir containing a dilutant such as a dilution buffer, wherein the metering structure (69), the conduit (72), the mixing arrangement (76), the dilutant reservoir and a conduit (78) connecting the dilutant reservoir to the discretization structure (2*b*), are arranged to obtain respective flow rates required for the desired mixing ratio. Additionally, the volumes of the discretization structures (2*a*) and (2*b*) are proportioned relative to each other in the ratio of the flow rate to synchronize the discrete volumes issuing from each discretization structure.

The intermediate chamber (34) of the mixing arrangement (76) is connected to a discretization structure (2*c*) of a mixing arrangement (82), instead of directly to the mixing chamber (30), by a conduit (80). A further dilutant reservoir is connected to a further discretization structure (2*d*) of the mixing arrangement (82) by a conduit (84) comprising a capillary valve (86). The capillary valve (86) defines a sudden change of the cross section and/or a localized surface modification in the path from the dilutant reservoir to the discretization structure (2*d*). Therefore, the conduit (84) is initially filled from the reservoir to the valve (86) and only begins to transport liquid to the discretization structure (2*d*) once a threshold rotational velocity is exceeded to break the surface tension barrier defined by the valve (86). The capillary valve (86) is designed to synchronize the arrival of liquid at the second mixing arrangement (82) from both the valve (86) and the first mixing arrangement (76). The further mixing arrangement (82) thus mixes, in a further stage, blood plasma diluted with dilutant from the mixing arrangement (76) with further dilutant. The common chamber (35) of the mixing arrangement (82) is connected by a second outlet to a mixing chamber (30), which thus receives the twice diluted solution.

The reservoirs supplying the discretization structures (2*b*) and (2*d*) are, in some embodiments, provided by an aliquoting structure connected to a common reservoir of a dilutant such as a buffer solution, for example PBS (phosphate buffered saline). The aliquoting structure is arranged to aliquote the required volume of dilutant during the initial separation step when the blood sample is separated by a separating arrangement (58), as described below.

The mixing chamber (30) comprises a connection (92) to an air system of the device or atmospheric air at one end and a capillary siphon structure (88), with operation as described above for the capillary siphon structure (74) at another end to maintain the diluted blood plasma inside the mixing chamber (30) until dilution is completed and then transfer the diluted sample to further structures of the device, for example, for sample retrieval or structures arranged for analysis of the sample, for example by optical detection.

The structures described above in relation to FIG. 10 are provided on a centrifugal microfluidics "lab on a disc" device (98) having a central cut-out 99 for engaging a drive mechanism and defining the center of rotation (4).

In a specific embodiment, the metering structure (69) is arranged to meter one microliter of blood plasma and the aliquoting structures feeding into the discretization structures (2*b*) and (2*d*) each meter 6 microliters of dilutant, so that the staged mixing structures (76) and (82) together provide a dilution of 1 microliter of plasma with 12 microliters of dilutant to achieve a dilution of 1:13 in the mixing chamber (30).

Figure 11:
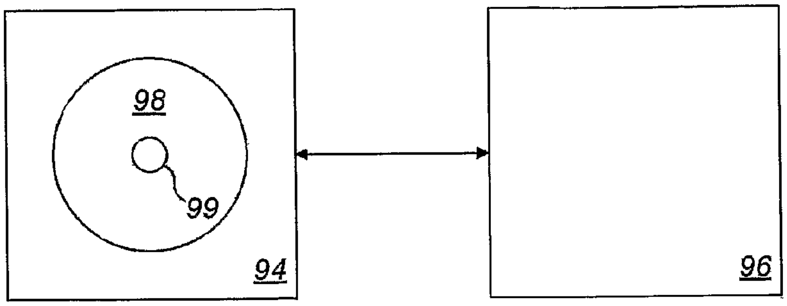
FIG. 11 illustrates a drive and control system for liquid processing using a device as described below with reference to the preceding figures.

With reference to FIG. 11, an analysis system using a centrifugal microfluidic device as described above, and in particular as described above with reference to FIG. 10 is now described. A drive system (94), under control of a control system (96) comprises means for driving a microfluidic centrifugal device such as the "lab on a disk" device (98) with controllable rotation speed sequences for fluidic processing of a sample loaded onto the device (98). In some embodiments the drive system (94) is coupled with analysis components for collecting data from the sample once it has been fluidicly processed in the device (98), and provide the data for the control system (96) for storage and/or further processing.

Figure 12:
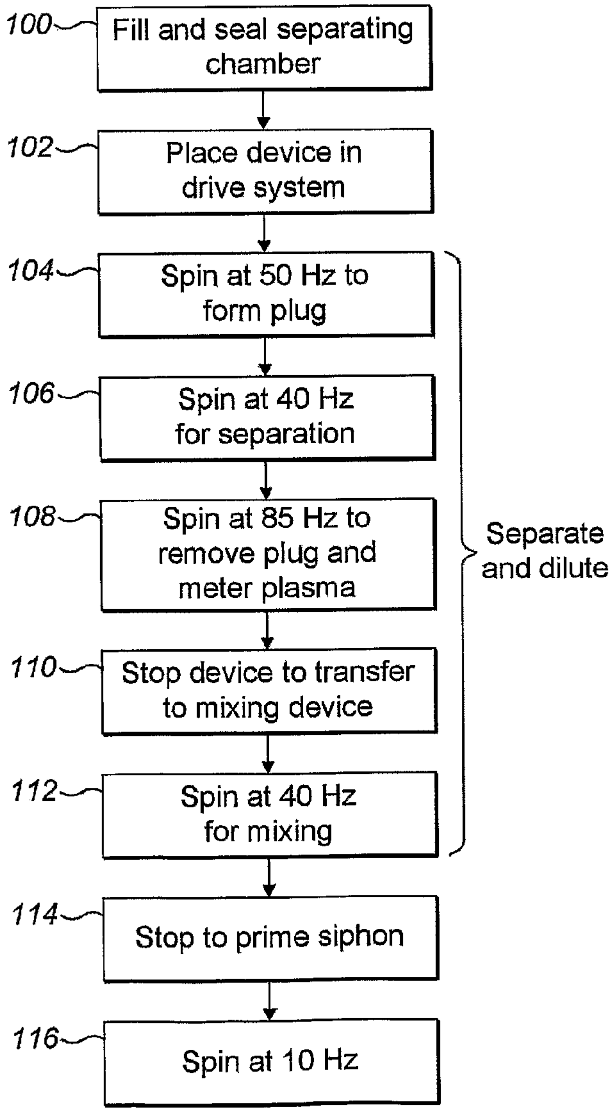
FIG. 12 depicts a frequency protocol for integrated blood separation and dilution using a device as described below with reference to FIG. 10.

With reference to FIG. 12, a method of processing a blood sample fluidically with a device as described above with reference to FIG. 10 is now described. At a first step (100), the separation chamber (60) is filled using the sample inlet (62) and the device is then sealed using an adhesive flap. The device is then placed in the drive system (step 102). In a first step (104) of a rotation protocol, the device is spun at a first frequency (e.g. 50 Hz) to form a plug inside the vent (68), as described above and in a second step (106) on the rotation protocol, the device continues to be spun at the same or a different frequency (e.g. 40 Hz) to separate plasma from cellular material. During step 104, the disk is accelerated at a given rate (e.g., 50 revolutions per/$s^2$) and maintained at that frequency for a given amount of time (e.g. 3 seconds). During step 106, the device is slowed to a given frequency (e.g. 40 Hz) at a given rate (e.g. 50 revolutions per/$s^2$) and the rotation frequency is maintained for a certain period (e.g. 60 seconds) in order to perform the separation of the cellular components from the blood plasma. Due to the plug formed in the vent (68) no blood is transferred from the separating chamber (60) to the receiving chamber (66) at this stage. At step 108, the rotation frequency is increased at a given rate (e.g. 5 revolutions per/$s^2$) up to a certain frequency (e.g. 85 Hz) enabling the removal of the liquid plug. Once a critical frequency is reached, the plug is ejected from the vent (68) and the (mostly) plasma flows into the receiving chamber (66). When the receiving chamber (66) is full, the plasma overflows to the plasma metering structure (69) and subsequently, any excess volume overflows and is collected in the overflow volume (70) to enable liquid metering. During part or all of steps 104 to 108, the dilutant is aliquoted by the aliquoting structure from the common reservoir into the two aliquotes as described above. The specific protocol and quantitative values of rotation frequency and rates of change given by example, are suitable to the particular embodiment described with reference to the figures. A person skilled in the art readily realises other protocols and parameter adjustments for different embodiments.

Since the conduits (72), (78) and (84) each comprise a capillary siphon structure no further flow occurs until the device is stopped (or nearly stopped to allow the capillary priming of the capillary siphon structures by overcoming the centrifugal pressure), starting the transfer to the mixing arrangements at step 110. Due to the capillary action of the respective conduits, the blood plasma advances up to a sudden expansion when it meets the discretization structure (2*a*), the dilutant in the conduit (78) advances until it meets a sudden expansion in a discretization structure (2*b*) and the dilutant in conduit (84) advances until it meets a sudden expansion in the capillary valve (86). The capillary valve (86) is positioned such that the time of transfer from it to the discretization structure (2*d*) corresponds to the time of transfer from the first mixing arrangement (76) to the discretization structure (2*c*), such that the once diluted liquid from the mixing arrangement (76) and the dilutant from the conduit (84) each reach the second mixing arrangements (82) in a synchronous fashion.

At step (112), the device is again spun at given rotation frequency (e.g. 40 Hz) to drive the respective liquids through the mixing arrangements (76) and (82), to ultimately mix in the mixing chamber (30). Once mixing is complete, the device is stopped or slowed again at step (114) to allow the capillary siphon (88) to be primed. The disk is then spun at a given rotation frequency (e.g. 10 Hz) at step (116) to transfer the diluted sample to further structures, such as the analysis structures mentioned above or, for example, a sample collection port.

In some embodiments, other discretization methods and structures than the "siphon" based one described above can be employed in single or cascaded mixing arrangements as described above. In fact, any structure providing for a certain accumulation capacity which can, for a given liquid propulsion mechanism, be partially or totally depleted at a faster rate than the accumulation rate can be equally employed.

Figure 13:
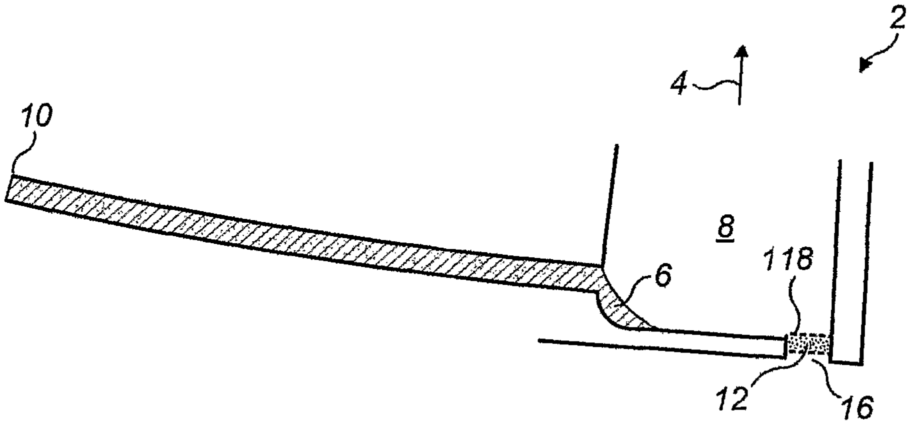
FIG. 13 illustrates a discretization structure based on a surface tension barrier.

In some embodiments, now described with reference to FIG. 13, the meandering outlet conduit described above is replaced with an outlet which represents a surface tension energy barrier to liquid flow through the outlet. These embodiments include the embodiments described above with the outlet structure suitably replaced. In some embodiments, the surface tension energy barrier is provided by a surface modification which renders the surface in the region of the outlet (16) hydrophobic (in embodiments manufactured from a material wetted by aqueous liquids for handling aqueous solutions, such as biological fluids) or, more generally, having a qualitatively different wetting behavior than surrounding surfaces. The modified surface is within the outlet conduit (12), as indicated by the dotted area (118) in FIG. 13 in some embodiments. In some embodiments, additionally or alternatively, the surface modification is present on a surface surrounding the entrance to the outlet conduit (12) to provide a surface tension energy prior to the outlet conduit (12).

In some embodiments, a surface tension energy barrier is provided by a sudden change in a dimension of the liquid conduit from the volume (8) through the outlet conduit (12), to which a front of a liquid column can attach. The sudden change is implemented, in some embodiments, by a step change in the depth of the discretization structure, at the entrance of the outlet conduit (12), inside the outlet conduit (12) or at the exit or outlet (16) of the outlet conduit (12). In the particular example of a structure manufactured from material wetted by aqueous liquids for handling aqueous liquids, the sudden change is a sudden expansion of one dimension, for example by configuring the outlet conduit (12) to be of capillary dimensions and to join with a surface surrounding its exit at a right or acute angle.

With all these surface tension based embodiments, as for the "siphon like" embodiments described above, the outlet conduit needs to be configured so that, once the discretization structure starts to empty, it empties at an outflow rate which is greater than the inflow rate, to ensure that the liquid column is eventually broken when the structure is substantially emptied and begins to fill again as the surface tension barrier is re-established. While the outlet is shown in a radially outward facing aspect of the discretization structure in FIG. 13*a* it could equally be provided in a side facing aspect of the discretization structure.

As the discretization structure (2) fills with liquid from the inlet structure, liquid is initially retained within the discretization structure by the surface tension energy barrier at the outlet conduit (12) and a liquid head starts to build up radially inward of the outlet conduit (12). As the liquid head rises as liquid flows into the disretisation structure (2), there comes a point when the liquid head has grown to a point where the driving force acting on it is sufficiently large to overcome the surface tension barrier so that liquid starts to cross the outlet conduit and flows at the outflow rate until the liquid volume is depleted and the surface tension barrier re-established.

The microfluidic devices as described above are, in some embodiments, fabricated by standard lithography procedures. One approach is the use of dry film photo-resists of different thicknesses to obtain a multiple depth structure. These films are laminated on transparent polymeric disk shaped substrates which have been provided with fluidic connections such as inlet and outlet ports by punching, milling or laser ablation. After developing and etching the structures, disk substrates are aligned and bonded by thermo-lamination. Specifically, the device described above for blood separation and dilution has, in some embodiments reservoir (including the discretization structures) and conduit depths of, respectively 120 and 55 micrometers. Other manufacturing techniques, are used in some embodiments and include direct laser ablation, CNC milling, hot-embossing, injection molding or injection/compression molding of PMMA (polymethyl methacrylate), PC (polycarbonate), PS (polystyrene), COP and COC (cyclocolefin polymers and co-polymers). After forming the fluid handling structure on one substrate, typically a bonding step is required to confine the fluid handling structure using a second substrate or film. Bonding of polymeric materials can be achieved by a variety of means including the use of adhesion promoting materials (e.g. liquid glues, solid adhesives, radiation curing, laser bonding, catalyst assisted bonding, solvent assisted bonding or thermally activated adhesion promoters), or through direct application of temperature provided there is intimate contact of the bonding surfaces. In particular, the microfluidic structures can be produced in one or both of two clear substrates, one clear and one darkly pigmented substrate or two darkly pigmented substrates depending on the analysis and detection applications performed subsequently to the microfluidic processing. In some embodiments, one of the halves can be at least partially metallized to facilitate certain optical detection processes, such as surface plasmon resonance detection.

In some embodiments, the volumes of the discretization structures in a mixing arrangement are both 60 nanoliters for a dilution of 1:2. For a dilution of 1:6, in some embodiments, one volume is 60 nanoliters and the other 300 nanoliters to achieve synchronized drop formation. In other embodiments, the same volumes are chosen for both discretization structures of a mixing arrangement, irrespective of mixing ratio, for example 60 nanoliter.

The above description of detailed embodiments of the invention is made by way of illustration and not for the purpose of limitation. In particular, many alterations, modifications and juxtapositions of the features described above will occur to the person skilled in the art and form part of the invention.

Other applications of discretization structures other than to mixing applications are equally envisaged. In particular, applications are not limited to the processing, separation and dilution of blood samples but many other applications will occur to the skilled person, such as the mixing of liquids in general. Furthermore, the discretization mechanisms and structures described are not limited to mixing purposes, and can be found advantageous in other applications where liquid droplets or plugs are necessary. For example, in some applications it is necessary to use discrete volumes of a first liquid are carried into a second imiscible liquid. The mixing mechanisms and structures described are not limited to two liquids, and can be further used with a single liquid or larger number of liquids.

The cascaded arrangement of FIG. 10 can be used with any type of discretization structure, as described or otherwise, and its supply structure can be different from the described arrangement for separating and aliquoting structures, for example including any combination of any one or more of separating structures, aliquoting structures and simple reservoirs. It is not limited to the processing of blood samples but is applicable to any other mixing or dilution application. Similarly, the processing of blood samples is not limited to the cascaded mixing arrangement, but single mixing arrangements can equally be used in this application. Other separating arrangements can be used in place of the one described above.

While the above description has been made in terms of a "threshold level" of the discretization structure, it will be understood that this is not limited to a flat, level filling of the discretization structure. For example, the surface of the volume in the discretization structure corresponding to the threshold level can be curved, due to surface tension effects, or the shape of the discretization structure and/or the centrifugal force acting on it. Similarly, the description has in some places been made in terms of parameters such as dimensions, frequencies, accelerations and time periods. It will be understood that these parameters are presented for the purposes of illustration. For example, the protocol described in reference to FIG. 12 is not limited to the specific values stated but is intended to extend to the general sequence of increasing and decreasing rotational frequencies of the steps described.

While the above description has been made in terms of centrifugal microfluidic devices, it will be understood that driving forces, other than centrifugal forces in a rotating device, can equally be employed with the principles described above. With the "siphon" based examples given above, a volume force, such as the centrifugal force, gravity or an electric force, or field for an electrically charged liquid are employed. A person skilled in the art will readily adapt the above considerations and in particular equations 1 to 6 for driving forces other than the centrifugal forces and the corresponding coordinate systems. Other discretization structures can be used with other driving forces, such as pressure differentials.

The invention is not limited to a microfluidic scale but applications on other, for example macroscopic scales are equally envisaged. For the avoidance of doubt, the term "microfluidic" is referred to herein to mean devices having a fluidic element such as a reservoir or a channel with at least one dimension below 1 mm.

The invention claimed is:

1. A device for containing liquid, the device comprising:

a first discretization structure; and a first supply structure for supplying, in response to a driving force, a first liquid at a first inflow rate to the first discretization structure;

the first discretization structure being shaped to define a first outlet and a first threshold level to which the first discretization structure fills with the first liquid before dispensing the first liquid, in response to the driving force, at a first outflow rate through the first outlet, the outlet being spaced from the first threshold level in the direction of the driving force;

wherein the first outflow rate is greater than the first inflow rate, thereby periodically emptying the first discretization structure to create a discretized flow of the first liquid from the first outlet in response to the driving force.

2. A device as claimed in claim 1, wherein the first discretization structure comprises a conduit in fluidic communication with the first supply structure at one end and defining the first outlet at the other end, the conduit comprising a bend between the two ends defining the threshold level, the one end being closer to the bend than the other end.

3. A device as claimed in claim 2, wherein the conduit comprises a further bend between the one end and the bend and the first discretization structure comprises a volume in fluidic communication with the supply structure and, through a port disposed to allow complete emptying of the volume through the conduit, in fluidic communication with the one end of the conduit.

4. A device as claimed in claim 2, the device being adapted for rotation about an axis, the one end being radially outward of the bend and the other end being radially outward of the one end.

5. A device as claimed in claim 3, arranged for rotation about an axis, the one end being radially outward of the bend and the other end and further bend being radially outward of the one end; the port being located at a radially outmost aspect of the volume.

6. A device as claimed in claim 1, wherein the first outlet is configured to provide a surface tension energy barrier to flow of the liquid, thereby retaining liquid in the discretization structure until the liquid reaches the first threshold level.

7. A device as claimed in claim 6, wherein liquid flowing through the first outlet experiences a sudden change in at least one dimension of the outlet to anchor a front of the liquid or by modifying the surface properties of the structure within or adjacent the outlet.

8. A device as claimed in claim 7, wherein the sudden change in at least one dimension is a sudden expansion.

9. A device as claimed in claim 6, wherein the discretization structure comprises a modified surface region of differing surface properties to an adjacent surface region within or adjacent the first outlet.

10. A device as claimed in claim 9, wherein the modified surface region is hydrophobic and the adjacent surface region is wetted by an aqueous liquid.

11. A device as claimed in claim 1, the device further comprising:

a second discretization structure;

a second supply structure for supplying, in response to a driving force, a second liquid at a second inflow rate to the second discretization structure; and a mixing chamber, the second discretization structure being shaped to define a second outlet and a second threshold level to which the second discretization structure fills with the second liquid before dispensing the second liquid, in response to the driving force, at a second outflow rate, greater than the second inflow rate, through the second outlet;

wherein the first and second outlets are in fluidic communication with the mixing chamber for receiving the first and second liquids, thereby allowing the liquids to mix.

12. A device as claimed in claim 11, wherein the first and second discretization structures are in fluidic communication with one another inside a common volume which, in use when the first and second supply structures are filled with the respective liquid, is only vented through the mixing chamber.

13. A device as claimed in claim 11, comprising an intermediate chamber in fluidic communication with the first and second outlets and having a single outlet in fluidic communication with the mixing chamber.

14. A device as claimed in claim 13, wherein the intermediate chamber defines a bubble removing feature adjacent the first outlet, arranged to capture liquid membranes formed at the first outlet after interruption of flow of the first liquid as the second liquid flows into the intermediate chamber.

15. A device as claimed in claim 14, wherein the feature is further arranged to guide bubbles formed by capturing of successively formed membranes away from the first outlet.

16. A device as claimed in claim 15, wherein the feature has a corner adjacent the first outlet disposed to be contactable by liquid issued from the second outlet and extending away from the first outlet of the first discretization structure to define a channel for guiding bubbles away from the corner.

17. A device as claimed in claim 16, wherein the channel widens with distance from the corner.

18. A device as claimed in claim 11, wherein the first and second supply structures are configured such that the first and second inflow rates form a ratio corresponding to a predetermined mixing ratio.

19. A device as claimed in claim 18, wherein the discretization structures are shaped such that a volume issued from the first outlet when the first liquid reaches the first threshold level and a volume issued from the second outlet when the second liquid reaches the second threshold level form a ratio corresponding to the predetermined mixing ratio.

20. A device as claimed in claim 18, wherein the first and second supply structures each comprise a reservoir shaped such that the respective liquid heads change at the same rate when each reservoir is emptied at the corresponding inflow rate.

21. A device as claimed in claim 11, the device further comprising:

a third discretization structure;

a third supply structure for supplying, in response to a driving force, a third liquid at a third inflow rate to the third discretization structure, the third discretization structure being shaped to define a third outlet and a third threshold level to which the third discretization structure fills with the third liquid before dispensing the third liquid, in response to the driving force, at a third outflow rate, greater than the third inflow rate, through the third outlet; and a fourth discretization structure, wherein the first and second outlets are in fluidic communication with the fourth discretization structure, the fourth discretization structure being shaped to define a fourth outlet and a fourth threshold level to which the fourth discretization structure fills with the first and second liquid before dispensing the first and second liquids, in response to the driving force, at a fourth outflow rate, greater than the fourth inflow rate, through the fourth outlet; and wherein the third and fourth outlets are in fluidic communication with the mixing chamber for receiving the first, second and third liquids, thereby allowing the liquids to mix.

22. A device as claimed in claim 21 wherein the first and second supply structures each define an interface with the corresponding discretization structure such that fluid flow stops at the interface when the driving force is not applied to the liquid; and the third supply structure comprises blocking means for releasably blocking liquid flow to the third discretization structure when the driving force is not applied to the liquid and a conduit connecting the blocking means to the third discretization structure; wherein the conduit is arranged such that when the driving force is applied the transit time of the third liquid from the blocking means to the third discretization structure is substantially the same as the transit time of the first and second liquids from the interface to the fourth discretization structure.

23. A device as claimed in claim 21, wherein the second and third supply structures include a common aliquoting structure for aliquoting respective volumes of the second and third liquid from a common reservoir.

24. A device as claimed in claim 11, wherein the first liquid is blood plasma and the first supply structure comprises means for receiving a blood sample and separating the blood plasma from the blood sample.

25. A device as claimed in claim 1, wherein the device is a microfluidic device.

26. A device as claimed in claim 1, wherein the device defines an axis of rotation and is rotatable about the axis to provide the driving force.

27. A device as claimed in claim 1, wherein the device is disc-shaped.

* * * * *